United States Patent
Takei et al.

(10) Patent No.: US 7,815,434 B2
(45) Date of Patent: Oct. 19, 2010

(54) DENTAL COATING KIT

(75) Inventors: Mitsuru Takei, Okayama (JP); Junichi Ohtsuki, Okayama (JP)

(73) Assignee: Kuraray Medical Inc., Kurashiki-shi (JP)

( * ) Notice: Subject to any disclaimer, the term of this patent is extended or adjusted under 35 U.S.C. 154(b) by 695 days.

(21) Appl. No.: 10/530,558

(22) PCT Filed: Oct. 6, 2003

(86) PCT No.: PCT/JP03/12798

§ 371 (c)(1),
(2), (4) Date: Apr. 7, 2005

(87) PCT Pub. No.: WO2004/032884

PCT Pub. Date: Apr. 22, 2004

(65) Prior Publication Data

US 2006/0078510 A1 Apr. 13, 2006

(30) Foreign Application Priority Data

Oct. 8, 2002 (JP) .............................. 2002-294821
Dec. 18, 2002 (JP) .............................. 2002-366253

(51) Int. Cl.
*A61K 6/00* (2006.01)
*A61K 6/02* (2006.01)
*A61K 6/08* (2006.01)

(52) U.S. Cl. ..................... 433/215; 433/226; 433/228.1; 523/115; 523/118; 522/1; 522/182; 106/35

(58) Field of Classification Search ................ 523/115, 523/118; 433/215, 226, 228.1; 522/1
See application file for complete search history.

(56) References Cited

U.S. PATENT DOCUMENTS 5,530,038 A * 6/1996 Yamamoto et al. .......... 523/116
6,174,935 B1 * 1/2001 Matsunae et al. ........... 523/118
6,251,963 B1 * 6/2001 Kohler et al. ................ 522/64

FOREIGN PATENT DOCUMENTS

| EP | 0 173 567 | * | 3/1986 |
| EP | 0 980 682 | * | 2/2000 |
| GB | 2332911 | | 7/1999 |
| JP | 11-180816 | | 7/1999 |
| JP | 2000-016911 | | 1/2000 |
| JP | 2001-271009 | | 10/2001 |
| JP | 2002-3327 | | 1/2002 |
| JP | 2002-003327 | * | 1/2002 |
| JP | 2003-040722 | | 2/2003 |

* cited by examiner

*Primary Examiner*—Frederick Krass
*Assistant Examiner*—Lezah W Roberts
(74) *Attorney, Agent, or Firm*—Oblon, Spivak, McClelland, Maier & Neustadt, L.L.P.

(57) ABSTRACT

The invention provides a dental coating kit with high adhesiveness to teeth that contains a primer composition including an acidic group-containing polymeric monomer (a), water (b) and a water-soluble solvent (c) and a surface smoothing composition including a polyfunctional polymeric monomer (f), a volatile solvent (g) and a photopolymerization initiator (h); and a dental coating kit with high adhesiveness to teeth and minimally suffering from chipping and peeling off that contains a primer composition including an acidic group-containing polymeric monomer (a), water (b) and a water-soluble solvent (c), a coating composition including a polymeric monomer (d) and a photopolymerization initiator (e), and a surface smoothing composition including a polyfunctional polymeric monomer (f), a volatile solvent (g) and a photopolymerization initiator (h). Either dental coating kit is particularly useful as a kit for preventing stain and color return of a bleached tooth.

7 Claims, No Drawings

DENTAL COATING KIT

TECHNICAL FIELD

The present invention relates to a dental coating kit, and more particularly, it relates to a coating kit useful for preventing stain and color change of teeth and in particular, a coating kit useful for preventing stain and color return of bleached teeth.

BACKGROUND ART

Teeth are stained or changed in color due to deposit of a colored substance included in a cigarette, coffee and the like, or breeding of chromogenic bacteria. In general, women wish to make their teeth look white and beautiful by preventing the stain and color change of the teeth more strongly than men. This is the reason why the number of women, and particularly young women, that receive a bleaching treatment for teeth described below is recently rapidly increasing.

The bleaching treatment for teeth is carried out not only as a part of beauty culture for making teeth look white and beautiful but also as means for restoring stained or color-changed teeth to former natural teeth. In the bleaching treatment, a bleaching agent including, as a principal component, hydrogen peroxide or urea peroxide is generally used. The bleaching agent has two functions, that is, a decoloring function to decompose a coloring matter deposited on teeth and a function to attain whiteness by roughening the surfaces of teeth for causing diffuse reflection of light. Owing to these two functions, the teeth can be made to look white. Although the bleaching treatment is effective for improving the aesthetic property, plaque, protein, a coloring matter and the like tend to adhere to the teeth after the bleaching treatment because the surfaces of the teeth are roughened. Therefore, for a while after the bleaching treatment, particularly for a couple of days after the bleaching, it is necessary to refrain from ingesting coffee, curry and citrus fruit juice and smoking, which can be a cause of stain. Even when the ingestion and smoking are thus restricted, however, the teeth may be stained in a short period of time. Also, plaque, protein, a coloring matter and the like are gradually accumulated on the teeth, or the surfaces of the teeth having been roughened through the bleaching treatment are gradually naturally restored due to remineralization caused by saliva in the oral cavity, and therefore, the bleached color is frequently returned to the former color prior to the bleaching treatment in approximately a half or two years after the bleaching.

In order to suppress the stain and the color return of teeth occurring after the bleaching, application of a finishing coating composition to teeth after the bleaching treatment is conventionally proposed. As such a finishing coating composition, for example, a composition including 10 wt % through 80 wt % of a polyfunctional acrylate monomer, 20 wt % through 80 wt % of a low-boiling solvent and 0.4 wt % through 5 wt % of a visible light-initiated polymerization initiator is proposed in Japanese Laid-Open Patent Publication No. 2001-271009, and a composition including 10 wt % through 80 wt % of a polyfunctional acrylate monomer, 20 wt % through 80 wt % of a low-boiling solvent, 0.4 wt % through 5 wt % of a visible light-initiated polymerization initiator and 0.5 wt % through 10 wt % of a white inorganic impalpable powder is proposed in Japanese Laid-Open Patent Publication No. 2002-3327.

Both of these compositions are, however, poor at adhesiveness to teeth. As a countermeasure against this disadvantage, addition of 0.1 wt % through 5 wt % of a phosphoric ester adhesive monomer to each composition is proposed (see Japanese Laid-Open Patent Publication No. 2001-271009, claim 8, [0030] and [0031]; and Japanese Laid-Open Patent Publication No. 2002-3327, claim 10, [0039] and [0040]).

The present inventors have, however, found the following: Even when a given amount of phosphoric ester adhesive monomer is added, the adhesiveness to teeth is not largely improved but the surface curing property is largely degraded. Therefore, it is difficult to thus obtain a practically usable coating composition.

The present invention was devised to overcome the aforementioned problem, and an object is providing a dental coating kit that is good at adhesiveness to teeth and is useful for preventing stain and color change of teeth.

DISCLOSURE OF INVENTION

In order to achieve the object, the dental coating kit (hereinafter sometimes referred to as the "first kit") of this invention includes a primer composition including an acidic group-containing polymeric monomer (a), water (b) and a water-soluble solvent (c); and a surface smoothing composition including a polyfunctional polymeric monomer (f), a volatile solvent (g) and a photopolymerization initiator (h).

The primer composition used in this invention is one generally designated as a self-etching type primer, and permeates into teeth while etching them so as to exhibit high adhesiveness. In particular, it deeply permeates into roughened teeth obtained after bleaching so as to exhibit very high adhesiveness. Since the adhesiveness to teeth is secured by the primer composition, there is no need to add a phosphoric ester adhesive monomer to the surface smoothing composition applied after the application of the primer composition. In the case where a phosphoric ester adhesive monomer is not added to the surface smoothing composition, a kit good not only at adhesiveness to teeth owing to the primer composition but also at surface curing property is obtained.

The primer composition used in the invention includes an acidic group-containing polymeric monomer (a), water (b) and a water-soluble solvent (c).

The acidic group-containing polymeric monomer (a) secures the adhesiveness to teeth. The acidic group-containing polymeric monomer (a) is a polymeric monomer that has an acidic group such as a phosphoric group, a pyrophosphoric group, a thiophosphoric group, a carboxylic group or a sulfonic group and also has a polymerizable unsaturated group such as an acryloyl group, a methacryloyl group, a vinyl group or a vinylbenzyl group. In particular, a polymeric monomer having an acryloyl group or a methacryloyl group as the unsaturated group is preferred.

Also, in the acidic group-containing polymeric monomer (a), the solubility of its calcium salt in water at 25° C. is preferably 10 wt % or less, more preferably 1 wt % or less and most preferably 0.1 wt % or less because such a polymeric monomer is good at adhesiveness and acid resistance. Specific examples of the acidic group-containing polymeric monomer (a) are described below. Hereinafter, methacryl and acryl are sometimes comprehensively mentioned as (meth) acryl and methacryloyl and acryloyl are sometimes comprehensively mentioned as (meth)acryloyl.

Examples of a phosphoric group-containing polymeric monomer are 2-(meth)acryloyloxyethyl dihydrogenphosphate, 3-(meth)acryloyloxypropyl dihydrogenphosphate, 4-(meth)acryloyloxybutyl dihydrogenphosphate, 5-(meth) acryloyloxypentyl dihydrogenphosphate, 6-(meth)acryloyl-hexyl dihydrogenphosphate, 7-(meth)acryloyloxyheptyl dihydrogenphosphate, 8-(meth)acryloyloxyoctyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 20-(meth)acryloyloxyeicosyl dihydrogenphosphate, 4-[2-(meth)acryloyloxyethyl]cyclohexyloxy dihydrogenphosphate, di[2-(meth)acryloyloxyethyl]hydrogenphosphate, di[3-(meth)acryloyloxypropyl]hydrogenphosphate, di[4-(meth)acryloyloxybutyl]hydrogenphosphate, di[5-(meth)acryloyloxypentyl]hydrogenphosphate, di[6-(meth)acryloyloxyhexyl]hydrogenphosphate, di[7-(meth)acryloyloxyheptyl]hydrogenphosphate, di[8-(meth)acryloyloxyoctyl]hydrogenphosphate, di[9-(meth)acryloyloxynonyl]hydrogenphosphate, di[10-(meth)acryloyloxydecyl hydrogenphosphate, 2-(meth)acryloyloxyethyl phenyl hydrogenphosphate, 2-(meth)acryloyloxyethyl hexyl hydrogenphosphate, 2-(meth)acryloyloxyethyl 2'-bromooctyl hydrogenphosphate, 2-(meth)acryloyloxyethyl octyl hydrogenphosphate, 2-(meth)acryloyloxyethyl nonyl hydrogenphosphate, 2-(meth)acryloyloxyethyl decyl hydrogenphosphate, 2-(meth)acryloyloxybutyl decyl hydrogenphosphate, (meth)acryloyloxyethyl phenyl phosphonate; (8-methacryloxy)octyl-3-phosphonopropionate, (9-methacryloxy)nonyl-3-phosphonopropionate, (10-methacryloxy)decyl-3-phosphonopropionate, (6-methacryloxy)octyl-3-phosphonoacetate, (10-methacryloxy)decyl-3-phosphonoacetate; 2-methacryloyloxyethyl (4-methoxyphenyl) hydrogenphosphate, 2-methacryloyloxypropyl (4-methoxyphenyl) hydrogenphosphate, and phosphoric group-containing hydrophobic polymeric monomers and their acid chlorides described in Japanese Laid-Open Patent Publication No. Sho 52-113089, Japanese Laid-Open Patent Publication No. Sho 53-67740, Japanese Laid-Open Patent Publication No. Sho 53-69494, Japanese Laid-Open Patent Publication No. Sho 53-144939, Japanese Laid-Open Patent Publication No. Sho 58-128393 and Japanese Laid-Open Patent Publication No. Sho 58-192891. In addition, the examples are alkali metal salts (such as sodium salt, potassium salt and lithium salt) and an ammonium salt of each of the aforementioned phosphoric group-containing polymeric monomers.

Examples of a pyrophosphoric group-containing polymeric monomer are di[2-(meth)acryloyloxyethyl]pyrophosphate, di[3-(meth)acryloyloxypropyl]pyrophosphate, di[4-(meth)acryloyloxybutyl]pyrophosphate, di[5-(meth)acryloyloxypentyl]pyrophosphate, di[6-(meth)acryloyloxyhexyl]pyrophosphate, di[7-(meth)acryloyloxyheptyl]pyrophosphate, di[8-(meth)acryloyloxyoctyl]pyrophosphate, di[9-(meth)acryloyloxynonyl]pyrophosphate, di[10-(meth)acryloyloxydecyl]pyrophosphate, di[12-(meth)acryloyloxydodecyl]pyrophosphate, and their acid chlorides, alkali metal salts and ammonium salts.

Examples of a thiophosphoric group-containing polymeric monomer are 2-(meth)acryloyloxyethyl dihydrogendithiophosphate, 3-(meth)acryloyloxypropyl dihydrogendithiophosphate, 4-(meth)acryloyloxybutyl dihydrogendithiophosphate, 5-(meth)acryloyloxypentyl dihydrogendithiophosphate, 6-(meth)acryloyloxyhexyl dihydrogendithiophosphate, 7-(meth)acryloyloxyheptyl dihydrogendithiophosphate, 8-(meth)acryloyloxyoctyl dihydrogendithiophosphate, 9-(meth)acryloyloxynonyl dihydrogendithiophosphate, 10-(meth)acryloyloxydecyl dihydrogenthiophosphate, and their acid chlorides, alkali metal salts and ammonium salts.

Examples of a carboxylic group-containing polymeric monomer are 4-(meth)acryloyloxyethyloxycarbonylphthalic acid, 4-(meth)acryloyloxybutyloxycarbonylphthalic acid, 4-(meth)acryloyloxyoctyloxycarbonylphthalic acid, 4-(meth)acryloyloxydecyloxycarbonylphthalic acid, and their acid anhydrides, 6-(meth)acryloylaminohexylcarboxylic acid, 8-(meth)acryloylaminooctylcarboxylic acid, 9-(meth)acryloyloxy-1,1-nonanedicarboxylic acid, 10-(meth)acryloyloxy-1,1-decanedicarboxylic acid, 11-(meth)acryloyloxy-1,1-undecanedicarboxylic acid, (meth)acrylic acid, maleic acid, and their acid chlorides, alkali metal salts and ammonium salts.

Examples of a sulfonic group-containing polymeric monomer are compounds having a sulfonic group such as 2-(meth)acrylamidoethyl sulfonic acid, 3-(meth)acrylamidopropyl sulfonic acid, 4-(meth)acrylamidobutyl sulfonic acid, 6-(meth)acrylamidohexyl sulfonic acid, 8-(meth)acrylamidooctyl sulfonic acid, 10-(meth)acrylamidodecyl sulfonic acid and styrene sulfonic acid, and their acid chlorides, alkali metal salts and ammonium salts.

As the acidic group-containing polymeric monomer (a), the phosphoric group-containing polymeric monomers are preferably used because of their high adhesiveness. In particular, a phosphoric group-containing polymeric monomer having an alkylene group with a carbon number of 6 through 25 and a phosphoric group-containing polymeric monomer having an alkyl group and/or a phenyl group are more preferably used, and a phosphoric group-containing polymeric monomer having an alkylene group with a carbon number of 6 through 12 is most preferably used.

One of these acidic group-containing polymeric monomers (a) may be singly used, or two or more of them may be used together if necessary. The adhesive strength to teeth may be lowered when the acidic group-containing polymeric monomer (a) is deficiently or excessively included. The mixing ratio of the acidic group-containing polymeric monomer (a) is generally 1 wt % through 90 wt %, preferably 5 wt % through 70 wt % and more preferably 10 wt % through 50 wt % based on a total weight of the primer composition.

The water (b) increases the demineralization against teeth of the acidic group-containing polymeric monomer (a). It is necessary to use water that includes substantially no impurity harmfully affecting the adhesiveness. Distilled water or ion-exchanged water is preferably used. The adhesive strength to teeth may be lowered when the water (b) is deficiently or excessively included. The mixing ratio of the water (b) is generally 0.1 wt % through 90 wt %, preferably 1 wt % through 70 wt % and more preferably 5 wt % through 50 wt % based on the total weight of the primer composition.

The water-soluble solvent (c) improves the permeability to teeth. A solvent that can dissolve the acidic group-containing polymeric monomer (a) and that can be dissolved in water at 25° C. at solubility of 5 wt % or more, preferably 30 wt % or more and more preferably in an arbitrary ratio is used. Examples of the water-soluble solvent (c) are a water-soluble volatile solvent (c-1) having a boiling point at normal pressure of 150° C. or less and preferably 100° C. or less, a water-soluble solvent (c-2) having a boiling point higher than 150° C. at normal pressure, and a water-soluble solvent (c-3) having a polymerizable unsaturated group and solubility in water at 25° C. of 10 wt % or more (hereinafter sometimes referred to as the "hydrophilic polymeric monomer (c-3)").

Examples of the water-soluble volatile solvent (c-1) are ethanol, methanol, 1-propanol, isopropyl alcohol, acetone, methyl ethyl ketone, 1,2-dimethoxyethane, 1,2-diethoxyethane and tetrahydrofuran.

Examples of the water-soluble solvent (c-2) are dimethyl sulfoxide, ethylene glycol and polyethylene glycol.

Examples of the hydrophilic polymeric monomer (c-3) are 2-hydroxyethyl (meth)acrylate, 2-hydroxypropyl (meth)acrylate, 3-hydroxypropyl (meth)acrylate, 1,3-dihydroxypropyl (meth)acrylate, 2,3-dihydroxypropyl (meth)acrylate, 2-trimethylammoniumethyl (meth)acryl chloride, (meth)acrylamide, 2-hydroxyethyl (meth)acrylamide and polyethylene glycol di(meth)acrylate (having nine or more oxyethylene groups).

Among the aforementioned water-soluble solvents (c), the water-soluble volatile solvent (c-1) and the hydrophilic polymeric monomer (c-3) are preferred. The water-soluble volatile solvent (c-1) is preferred because it can be easily perspired with a dental air syringe. Also, the hydrophilic polymeric monomer (c-3) is preferred because it can be cured simultaneously with the acidic group-containing polymeric monomer (a). Among the aforementioned examples of the hydrophilic polymeric monomer (c-3), 2-hydroxyethyl (meth)acrylate, 2-hydroxypropyl (meth)acrylate, 3-hydroxypropyl (meth)acrylate, 1,3-dihydroxypropyl (meth)acrylate, 2,3-dihydroxypropyl (meth)acrylate and polyethylene glycol di(meth)acrylate (having nine oxyethylene groups) are particularly preferred.

One of the water-soluble solvents (c) may be singly used, or two or more of them may be used together if necessary. The permeability to teeth and the adhesive strength may be lowered when the water-soluble solvent (c) is deficiently or excessively included. The mixing ratio of the water-soluble solvent (c) is generally 1 wt % through 98 wt %, preferably 5 wt % through 90 wt % and more preferably 10 wt % through 60 wt % based on the total weight of the primer composition.

In order to improve the adhesiveness, the mechanical strength and the coating property of the primer composition, a hydrophobic polymeric monomer with solubility in water at 25° C. of less than 10 wt % and preferably of 1 wt % or less may be included apart from the acidic group-containing polymeric monomer (a) and the hydrophilic polymeric monomer (c-3). Examples of such a hydrophobic polymeric monomer are esters such as α-cyanoacrylic ester, (meth)acrylic ester, α-halogenoacrylic acid ester, crotonic ester, cinnamic ester, sorbic ester, maleic ester and itaconic ester, a (meth)acrylamide derivative, vinyl esters, vinyl ethers, a mono-N-vinyl derivative and a styrene derivative. Among these monomers, (meth)acrylic ester is preferred.

Now, specific examples of the (meth)acrylic ester will be described. A monomer having n (wherein n=1, 2, 3, etc.) olefin double bonds is expressed as an n-functional monomer, and the examples are divided into three groups of mono-functional monomers, bifunctional monomers, and monomers of trifunctional or higher functionality.

Mono-functional monomers:
methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth) acrylate, 2,3-dibromopropyl (meth)acrylate, 3-methacryloyloxypropyltrimethoxysilane, 11-methacryloyloxyundecyltrimethoxysilane Bifunctional monomers:
ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, bisphenol A diglycidyl (meth)acrylate, 2,2-bis[4-(meth)acryloyloxyethoxyphenyl]propane, 2,2-bis[4-(meth)acryloyloxypolyethoxyphenyl]propane, 2,2-bis[4-[3- (meth)acryloyloxy-2-hydroxypropoxy]phenyl]propane, 1,2-bis [3- (meth)acryloyloxy-2-hydroxypropoxy]ethane, 1,2-bis(3-methacryloyloxy-2-hydroxypropoxy)ethane, [2,2,4-trimethylhexamethylene bis(2-carbamoyloxyethyl)] dimethacrylate Monomers of trifunctional or higher functionality:
trimethylolpropane tri(meth)acrylate, trimethylolethane tri(meth)acrylate, tetramethylolmethane tri(meth)acrylate, N,N'-(2,2,4-trimethylhexamethylene) bis[2-(aminocarboxy) propane-1,3-diol]tetra(meth)acrylate, pentaerythritol tri (meth)acrylate, pentaerythritol tetra(meth)acrylate, dipentaerythritol tetra(meth)acrylate, dipentaerythritol penta (meth)acrylate, dipentaerythritol hexa(meth)acrylate One of these hydrophobic polymeric monomers may be singly used, or two or more of them may be used together if necessary. When the hydrophobic polymeric monomer is excessively included, the permeability to teeth and the adhesive strength may be lowered. The mixing ratio of the hydrophobic polymeric monomer is generally 70 wt % or less, preferably 50 wt % or less and more preferably 30 wt % or less based on the total weight of the primer composition.

In order to improve the adhesiveness, the primer composition may include a photopolymerization initiator and/or a chemical polymerization initiator. Examples of the photopolymerization initiator are α-diketones, ketals, thioxanthones, acylphosphine oxides and α-aminoacetophenones.

Examples of the α-diketones are camphorquinone, benzyl and 2,3-pentanedione.

Examples of the ketals are benzyl dimethyl ketal and benzyl diethyl ketal.

Examples of the thioxanthones are 2-chlorothioxanthone and 2,4-diethylthioxanthone.

Examples of the acylphosphine oxides are 2,4,6-trimethylbenzoyldiphenylphosphine oxide, bis(2,4,6-trimethylbenzoyl)phenylphosphine oxide, bis(benzoyl)phenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyldi-(2,6-dimethylphenyl) phosphonate, 2,4,6-trimethylbenzoylethoxyphenylphosphine oxide, and a water-soluble acylphosphine oxide compound disclosed in Japanese Patent Publication No. Hei 3-57916.

Examples of the α-aminoacetophenones are 2-benzyl-dimethylamino-1-(4-morpholinophenyl)-butanone-1, 2-benzyl-diethylamino-1-(4-morpholinophenyl)-butanone-1, 2-benzyl-dimethylamino-1-(4-morpholinophenyl)-propanone-1, 2-benzyl-diethylamino-1-(4-morpholinophenyl)-propanone-1, 2-benzyl-dimethylamino-1-(4-morpholinophenyl)-pentanone-1, and 2-benzyl-diethylamino-1-(4-morpholinophenyl)-pentanone-1.

One of these photopolymerization initiators may be singly used, or two or more of them may be used together if necessary. The mixing ratio of the photopolymerization initiator is preferably 0.01 wt % through 10 wt %, more preferably 0.05 wt % through 7 wt % and most preferably 0.1 wt % through 5 wt % based on the total weight of the polymeric monomer(s) included in the primer composition.

The photopolymerization initiator may be used by itself or used together with a polymerization promoter such as a tertiary amine, an aldehyde or a compound having a thiol group for accelerating the photo-curing property.

Examples of the tertiary amine are 2-dimethylaminoethyl (meth)acrylate, N,N-bis[(meth)acryloyloxyethyl]-N-methylamine, ethyl 4-dimethylaminobenzoate, butyl 4-dimethylaminobenzoate, butoxyethyl 4-dimethylaminobenzoate, N-methyldiethanolamine, 4-dimethylaminobenzophenone and N,N-di(2-hydroxyethyl)-p-toluidine.

Examples of the aldehyde are dimethylaminobenzaldehyde and terephthalaldehyde.

Examples of the compound having a thiol group are 2-mercaptobenzoxazole, decanethiol, 3-mercaptopropyltrimethoxysilane and thiobenzoic acid.

One of these polymerization promoters may be singly used, or two or more of them may be used together if necessary. The mixing ratio of the polymerization promoter is preferably 0.01 wt % through 10 wt %, more preferably 0.05 wt % through 7 wt % and most preferably 0.1 wt % through 5 wt % based on the total weight of the polymeric monomer(s) included in the primer composition.

As the chemical polymerization initiator, a redox type polymerization initiator composed of an oxidizing agent and a reducing agent is preferably used. When the redox type polymerization initiator is used, it is necessary to divide packaging of the primer composition into two or more sections so that the oxidizing agent and the reducing agent can be spaced from each other.

Examples of the oxidizing agent are organic peroxides such as diacyl peroxides, peroxy esters, dialkyl peroxides, peroxy ketals, ketone peroxides and hydroperoxides.

Specific examples of the diacyl peroxides are benzoyl peroxide, 2,4-dichlorobenzoyl peroxide and m-toluoyl peroxide. Specific examples of the peroxy esters are t-butyl peroxybenzoate, bis-t-butyl peroxyisophthalate, 2,5-dimethyl-2,5-bis(benzoylperoxy)hexane, t-butyl peroxy-2-ethylhexanoate and t-butylperoxy isopropyl carbonate. Specific examples of the dialkyl peroxides are dicumyl peroxide, di-t-butyl peroxide and lauroyl peroxide. A specific example of the peroxy ketals is 1,1-bis(t-butylperoxy)-3,3,5-trimethylcyclohexane. Specific examples of the ketone peroxides are methyl ethyl ketone peroxide, cyclohexanone peroxide and methyl acetoacetate peroxide. Specific examples of the hydroperoxides are t-butyl hydroperoxide, cumene hydroperoxide and p-diisopropylbenzene peroxide.

As the reducing agent, an aromatic tertiary amine, an aliphatic tertiary amine, a sulfinic acid or its salt is preferably used.

Examples of the aromatic tertiary amine are N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-dibutylaniline, ethyl 4-dimethylaminobenzoate, n-butoxyethyl 4-dimethylaminobenzoate and (2-methacryloyloxy)ethyl 4-dimethylaminobenzoate.

Examples of the aliphatic tertiary amine are trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate and triethanolamine trimethacrylate.

Examples of the sulfinic acid and its salt are benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate and calcium 2,4,6-triisopropylbenzenesulfinate.

One of these oxidizing agents or these reducing agents may be singly used, or two or more of them may be used together if necessary. The mixing ratio of each of the oxidizing agent and the reducing agent is preferably 0.01 wt % through 10 wt %, more preferably 0.05 wt % through 7 wt % and most preferably 0.1 wt % through 5 wt % based on the total weight of the polymeric monomer(s) included in the primer composition.

In order to adjust the coating property and the flowability of the primer composition, it may include a filler. As the filler, an inorganic filler, an organic filler or an organo-mineral complex filler may be used.

As the inorganic filler, silica, a mineral including, as a matrix, silica such as kaoline, clay, isinglass or mica, and ceramics and glass including silica as a matrix and further including $Al_2O_3$, $B_2O_3$, $TiO_2$, $ZrO_2$, $BaO$, $La_2O_3$, $SrO_2$, $CaO$, $P_2O_5$ or the like are preferably used. Specific examples of such glass are lanthanum glass, barium glass, strontium glass, soda glass, lithium borosilicate glass, zinc glass, fluoroalumino silicate glass, borosilicate glass and bioglass. Apart from them, crystalline quartz, hydroxyl-apatite, alumina, titanium oxide, yttrium oxide, zirconia, calcium phosphate, barium sulfate, aluminum hydroxide, sodium fluoride, potassium fluoride, sodium monofluorophosphate, lithium fluoride or ytterbium fluoride is also preferably used.

Examples of the organic filler are polymethyl methacrylate, polymethyl methacrylate, a polymer of polyfunctional methacrylate, polyamide, polystyrene, polyvinyl chloride, chloroprene rubber, nitrile rubber and styrene-butadiene rubber.

Examples of the organo-mineral complex filler are a filler obtained by dispersing an inorganic filler in an organic filler and an inorganic filler coated with any of various polymeric monomers.

In order to adjust the flowability of the primer composition or to improve the coating property thereof, the filler may be subjected to surface-treating with a known surface-treatment agent such as a silane coupling agent before adding to the primer composition. Examples of the surface-treatment agent used in this case are vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane and γ-aminopropyltriethoxysilane.

One of these fillers may be singly used, or two or more of them may be used together if necessary. The mixing ratio of the filler is generally 50 wt % or less and preferably 30 wt % or less based on the total weight of the primer composition. When the mixing ratio exceeds 50 wt %, the permeability to teeth and the adhesiveness may be lowered.

Furthermore, in order to improve the demineralization of the primer composition against teeth, an acid that has smaller pKa than the acidic group-containing polymeric monomer (a) and does not have a polymeric group may be included in the primer composition. Examples of such an acid are inorganic acids such as phosphoric acid, nitric acid and sulfuric acid, and organic acids such as acetic acid, citric acid, trichloroacetic acid and p-toluenesulfonic acid. When such an acid having no polymeric group is excessively included, however, the acid may damage the dentine or be eluted after the application so as to lower the adhesiveness to teeth of the primer composition. Accordingly, in general, the mixing ratio of the acid is preferably 10 wt % or less and more preferably 5 wt % or less based on the total weight of the primer composition.

The primer composition may include a polymerization inhibitor, a coloring agent, a fluorescent agent, a ultraviolet absorbing agent and the like. Also, in order to provide antibacterial activity, an antibacterial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride or Triclosan may be included in the primer composition.

The surface smoothing composition used in this invention includes a polyfunctional polymeric monomer (f), a volatile solvent (g) and a photopolymerization initiator (h).

As the polyfunctional polymeric monomer (i), a hydrophobic polymeric monomer having two or more olefin double bonds is used. As such a hydrophobic polymeric monomer, any of the aforementioned bifunctional polymeric monomers and the polymeric monomers of trifunctional or higher functionality of (meth)acrylic ester to be included in the primer composition as an arbitrary component can be used. From the viewpoint of the surface curing property, a polymeric monomer having three or more olefin double bonds, such as pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate or dipentaerythritol hexa(meth)acrylate, is preferred, and a polymeric monomer having five or more olefin double bonds, such as dipentaerythritol penta(meth)acrylate or dipentaerythritol hexa(meth)acrylate, is particularly preferred. The polyfunctional polymeric monomer (f) includes a polymeric monomer having three or more olefin double bonds in a ratio of preferably 70 wt % or more and more preferably 80 wt % or more based on the total weight of the polyfunctional polymeric monomer (f).

The mixing ratio of the polyfunctional polymeric monomer (f) is preferably 40 wt % through 98 wt % and more preferably 80 wt % through 95 wt % based on the total weight of the surface smoothing composition. When the mixing ratio is smaller than 40 wt %, the coating property and the operability of the surface smoothing composition may be lowered.

The volatile solvent (g) dilutes the polyfunctional polymeric monomer (f) and improves the coating property and the operability of the surface smoothing composition. As the volatile solvent (g), one having a boiling point at normal pressure of 150° C. or less is preferably used and one having a boiling point of 100° C. or less is more preferably used. When a volatile solvent having a boiling point higher than 150° at normal pressure is used as the volatile solvent (g), the surface curing property of the surface smoothing composition may be lowered. Examples of the volatile solvent (g) are alcohols such as ethanol, methanol, 1-propanol and isopropyl alcohol, ketones such as acetone, methyl ethyl ketone and diethyl ketone, ethers such as 1,2-dimethoxyethane, 1,2-diethoxyethane and tetrahydrofuran, esters such as methyl formate, ethyl formate, methyl acetate, ethyl acetate, propyl acetate and butyl acetate, and (meth)acrylic esters such as methyl (meth)acrylate, ethyl (meth)acrylate, n-propyl (meth)acrylate and isopropyl (meth)acrylate. Among these solvents, the (meth)acrylic esters are preferred because they can be cured simultaneously with the polyfunctional polymeric monomer (f), and methyl methacrylate is particularly preferred because it has low toxicity and a low boiling point.

One of these volatile solvents (g) may be singly used, or two or more of them may be used together if necessary. From the viewpoint of the coating property and the operability, the mixing ratio of the volatile solvent (g) is preferably 1 wt % through 59 wt %, more preferably 5 wt % through 50 wt % and most preferably 10 wt % through 40 wt % based on the total weight of the surface smoothing composition. When the mixing ratio exceeds 59 wt %, the surface smoothing composition tends to have so high flowability that the operability and the coating property are degraded or to emit a strong odor in curing.

As the photopolymerization initiator (h), any of the aforementioned photopolymerization initiators to be included in the primer composition as an arbitrary component can be used. Among them, α-diketones and acylphosphine oxides are preferred. More preferably, 2,4,6-trimethylbenzoyldiphenylphosphine oxide is used because it is less colored and is less yellowed after curing.

One of these photopolymerization initiators (h) may be singly used, or two or more of them may be used together if necessary. The mixing ratio of the photopolymerization initiator (h) is preferably 0.01 wt % through 10 wt % and more preferably 1 wt % through 5 wt % based on the total weight of the polymeric monomer(s) included in the surface smoothing composition. The photopolymerization initiator (h) may be used by itself or used together with a polymerization promoter for accelerating the curing property. As such a polymerization promoter, any of the aforementioned polymerization promoters to be included in the primer composition as an arbitrary component can be used. The mixing ratio of the polymerization promoter is preferably 0.01 wt % through 10 wt %, more preferably 0.05 wt % through 7 wt % and most preferably 0.1 wt % through 5 wt % based on the total weight of the polymeric monomer(s) included in the surface smoothing composition.

The surface smoothing composition may include a pigment if necessary. When a pigment is included, the color tone of a resultant coating layer can be adjusted. Examples of such a pigment are blood red, phthalocyanine blue, various azo pigments and titanium oxide. For example, when the surface smoothing composition includes titanium oxide, the resultant composition attains an opaque property so as to cover the aesthetic property of the teeth. One of these pigments may be singly used, or two or more of them may be used together if necessary. The mixing ratio of the pigment is appropriately adjusted in consideration of the color tone of the coating layer and the aesthetic property.

The surface smoothing composition may include a filler if necessary. As the filler, any of the aforementioned fillers to be included in the primer composition as an arbitrary component can be used. One of these fillers may be singly used, or two or more of them may be used together if necessary. The mixing ratio of the filler is preferably 40 wt % or less and more preferably 20 wt % or less based on the total weight of the surface smoothing composition. When the mixing ratio exceeds 40 wt %, the coating property and the operability of the surface smoothing composition may be lowered. Also, as the filler, one with an average particle diameter of 0.01 μm through 50 μm is generally used, and when the surface smoothing composition includes a pigment, a ultrafine filler with a particle diameter of 0.001 μm through 0.1 μm is preferably used for effectively suppressing precipitation of the pigment. As such a ultrafine filler, colloidal silica (for example, trade name "Aerosil" manufactured by Japan Aerosil) is preferred. The surface smoothing composition may further include a polymerization inhibitor, a fluorescent agent, an ultraviolet absorbing agent and the like if necessary.

In the preparation of the surface smoothing composition, the respective components are preferably appropriately selected and blended so as to attain appropriate viscosity. From the viewpoint of the coating property and the operability, the viscosity of the surface smoothing composition at 30° C. is preferably 30 cP through 3,000 cP, more preferably 50 cP through 1,000 cP and most preferably 80 cP through 500 cP. When the viscosity is lower than 30 cP, the flowability is so high that the composition may permeate into a space between adjacent teeth in the application to the teeth, and when it exceeds 3,000 cP, the coating property may be lowered.

The first kit is useful particularly for preventing the stain and the color return of bleached teeth. Therefore, a method for using the first kit will now be described by exemplifying the case where bleached teeth are coated.

First, the primer composition is applied on the surfaces of the bleached teeth, and the thus coated layer is dried by using a dental air syringe if necessary until the primer composition loses its flowability, or in the case where the primer composition includes a polymerization initiator (a photopolymerization initiator and/or a chemical polymerization initiator), the coated layer is polymerically cured. Thus, a primer layer is formed (step 1).

Next, the surface smoothing composition is applied on the primer layer, and the applied surface smoothing composition is polymerically cured through light irradiation, so as to form a surface layer on the surfaces of the bleached teeth (step 2). In the case where the primer composition includes a photopolymerization initiator, the primer composition and the surface smoothing composition may be simultaneously polymerically cured through the light irradiation.

The thickness of the applied surface smoothing composition is preferably 0.005 mm through 0.5 mm and more preferably 0.01 mm through 0.3 mm. A preferable light source used for the light irradiation is, for example, a xenone lamp, a halogen lamp, a mercury lamp or a light emitting diode. The time of the light irradiation depends upon the wavelength and the amount of the light. When a dental irradiator is used, the composition can be cured in approximately 3 seconds through 3 minutes. After forming the coating layer on the bleached teeth, if a part or the whole of the coating layer is peeled off from the surfaces of the teeth or if any defect occurs owing to stain or the like, the defective portion is peeled off by using a dental instrument such as a scaler, and then the composition is applied on the teeth again. When the treatment is thus repeated, the stain and the color return of the teeth otherwise occurring after the bleaching can be effectively prevented.

The first kit can be used on teeth a part of which is restored with a restorative dental material such as a metal, porcelain, ceramics or a composite curing substance. Also, the first kit may be used by itself or may be used in combination with a commercially available dental metal primer, a primer for adhering porcelain or a tooth plane cleaning agent such as a sodium hypochlorite solution.

As described above, when the first kit is used, the adhesiveness to teeth can be secured owing to the primer composition, and therefore, a coating layer with high adhesiveness to teeth can be formed.

The first kit has, however, a problem to be solved that chipping (that is, a phenomenon that a small part of the coating layer is chipped and peeled off) and peeling off are easily caused in the coating layer by stress applied in biting because the layer (surface layer) made of the surface smoothing composition is hard and crumbly.

Another dental coating kit according to this invention (hereinafter sometimes referred to as the "second kit") overcomes the above-described disadvantage of the first kit.

Specifically, the second kit includes a primer composition composed of an acidic group-containing polymeric monomer (a), water (b) and a water-soluble solvent (c), a coating composition composed of a polymeric monomer (d) and a photopolymerization initiator (e), and a surface smoothing composition composed of a polyfunctional polymeric monomer (f), a volatile solvent (g) and a photopolymerization initiator (h).

The primer composition and the surface smoothing composition of the second kit are the same as those of the first kit described above.

Therefore, hereinafter, the coating composition included in the second kit alone will be described.

The coating composition is a composition used for forming an intermediate layer between a layer made of the primer composition (a primer layer) and a layer made of the surface smoothing composition (a surface layer). This intermediate layer functions as a buffer layer for preventing the chipping and peeling off of the uppermost layer made of the surface smoothing composition.

The coating composition includes a polymeric monomer (d) and a photopolymerization initiator (e).

The polymeric monomer (d) is not particularly specified as far as it can form the intermediate layer on the primer layer. The polymeric monomer (d) is appropriately selected in consideration of the viscosity and the polymerizing property of the resultant coating composition and the strength of the resultant coating layer. When the content of the polymeric monomer (d) is excessive, the coating property, the flowability, the operability and the like of the coating composition (II) may be lowered. Therefore, the content is preferably 40 through 99.99 wt % and more preferably 60 through 99.95 wt % based on the total weight of the coating composition.

One of polymeric monomers (d) may be singly used, or two or more of them may be used together if necessary. In particular, when a combination of a hydrophilic polymeric monomer and a hydrophobic polymeric monomer is used, a coating layer effectively usable as a buffer layer that is good at wettability and permeability to teeth and attains high tenacity after polymerically curing the composition can be obtained.

The hydrophilic polymeric monomer not only improves the wettability and the permeability to teeth but also increases the tenacity of the resultant coating layer. The tenacity is increased by using the hydrophilic polymeric monomer because a polymerically cured coating layer including the hydrophilic polymeric monomer absorbs water and swells in a humid environment in an oral cavity. The hydrophilic polymeric monomer herein means a polymeric monomer with solubility in water at 25° C. of 10 wt % or more. As the hydrophilic polymeric monomer, a polymeric monomer with the solubility of 30 wt % or more is preferably used.

Specific examples of the hydrophilic polymeric monomer are 2-hydroxyethyl (meth)acrylate, 2-hydroxypropyl (meth)acrylate, 3-hydroxypropyl (meth)acrylate, 1,3-dihydroxypropyl (meth)acrylate, 2,3-hydroxypropyl (meth)acrylate, 2-hydroxypropyl-1,3-di(meth)acrylate, 3-hydroxypropyl-1,2-di(meth)acrylate, pentaerythritol di(meth)acrylate, 2-trimethylammonium ethyl (meth)acryl chloride, (meth)acrylamide, 2-hydroxyethyl (meth)acrylamide and polyethylene glycol di(meth)acrylate (having nine or more oxyethylene groups). In particular, 2-hydroxyethyl methacrylate is preferred.

One of these hydrophilic polymeric monomers may be singly used, or two or more of them may be used together if necessary. The mixing ratio of the hydrophilic polymeric monomer is preferably 5 wt % through 50 wt % based on the total weight of the coating composition. When the mixing ratio is smaller than 5 wt %, the wettability of the coating composition or the tenacity of the resultant cured substance tend to be lowered, and when it exceeds 50 wt %, the strength of the resultant cured substance may be lowered. The mixing ratio is more preferably 5 wt % through 40 wt % and most preferably 10 wt % through 35 wt %.

The hydrophobic polymeric monomer improves the adhesiveness, the mechanical strength and the coating property. The hydrophobic polymeric monomer herein means a polymeric monomer with solubility in water at 25° C. of 10 wt % or less. As the hydrophobic polymeric monomer, a polymeric monomer with the solubility of 1 wt % or less is preferably used.

Specific examples of the hydrophobic polymeric monomer are esters such as (meth)acrylic ester, α-cyanoacrylic ester, α-acrylic acid ester halide, crotonic ester, cinnamic ester, sorbic ester, maleic ester and itaconic ester, and a compound having a polymerizable unsaturated group such as a (meth)acrylamide derivative, a vinyl ester, a vinyl ether, a mono-N-vinyl derivative or a styrene derivative. In particular, (meth)acrylic ester is preferred. As the (meth)acrylic ester, any of the aforementioned (meth)acrylic esters to be included in the primer composition as an arbitrary component can be used.

The kind of hydrophobic polymeric monomer is appropriately selected in consideration of the viscosity, the polymerizing property and the like of the coating composition. One of the hydrophobic polymeric monomers may be singly used, or two or more of them may be used together if necessary. From the viewpoint of the polymerizing property, a monomer of a bifunctional or higher functionality is preferably used. When the hydrophobic polymeric monomer is deficiently included, the coating property, the flowability and the operability of the coating composition may be lowered. The mixing ratio of the hydrophobic polymeric monomer is preferably 20 wt % through 90 wt % and more preferably 40 wt % through 80 wt % based on the total weight of the coating composition.

When a polymeric monomer (an acidic group-containing polymeric monomer) that has one or more acidic groups such as a phosphoric group, a pyrophosphoric group, a thiophosphoric group, a carboxylic group and a sulfonic group and also has a polymerizable unsaturated group such as an acryloyl group, a methacryloyl group, a vinyl group or a styrene group is included as the polymeric monomer (d) in addition to the hydrophilic polymeric monomer and the hydrophobic polymeric monomer, the adhesiveness to teeth can be further improved. From the viewpoint of the adhesiveness, the acidic group-containing polymeric monomer has solubility in water at 25° C. of preferably 10 wt % or less, more preferably 1 wt % or less and most preferably 0.1 wt % or less. As the acidic group-containing polymeric monomer, any of the aforementioned acidic group-containing polymeric monomers (a) to be included in the primer composition as an essential component can be used. As the acidic group-containing polymeric monomer, a phosphoric group-containing polymeric monomer is preferably used because of its high adhesiveness. In particular, a phosphoric group-containing polymeric monomer having an alkylene group with a carbon number of 6 through 25, an alkyl group and/or a phenyl group is more preferred, and a phosphoric group-containing polymeric monomer having an alkylene group with a carbon number of 6 through 12 is most preferred.

One of the acidic group-containing polymeric monomers may be singly used, or two or more of them may be used together if necessary. When the acidic group-containing polymeric monomer is excessively included, the polymerizing property (surface curing property) of the coating composition may be lowered. Therefore, the mixing ratio of the acidic group-containing polymeric monomer is preferably 0.1 wt % through 30 wt % and more preferably 0.1 wt % through 20 wt % based on the total weight of the coating composition.

As the photopolymerization initiator (e) included in the coating composition, any of known photopolymerization initiators can be used. For example, any of the aforementioned photopolymerization initiators to be included in the primer composition as an arbitrary component can be used as the photopolymerization initiator (e). One of the photopolymerization initiators may be singly used, or two or more of them may be used together if necessary. The mixing ratio of the photopolymerization initiator (e) is preferably 0.01 wt % through 10 wt %, more preferably 0.05 wt % through 7 wt % and most preferably 0.1 wt % through 5 wt % based on the polymeric monomer (d).

In order to accelerate the photo-setting property, the photopolymerization initiator (e) may be used together with a polymerization promoter. As the polymerization promoter, for example, any of the aforementioned tertiary amines, aldehydes and compounds having thiol to be included in the primer composition as an arbitrary component can be used. One of these compounds may be singly used, or two or more of them may be used together if necessary. The content of the polymerization promoter is preferably 0.01 wt % through 10 wt %, more preferably 0.05 wt % through 7 wt % and most preferably 0.1 wt % through 5 wt % based on the total weight of the coating composition.

If necessary, the photopolymerization initiator (e) may be used together with a chemical polymerization initiator. When the chemical polymerization initiator is used together, the polymerizing property in an inside portion of the coating layer, which is difficult to photopolymerize because light minimally reaches it, can be improved. As such a chemical polymerization initiator, a redox type chemical polymerization initiator composed of an oxidizing agent and a reducing agent is preferably used. When the redox type chemical polymerization initiator is used, it is necessary to divide packaging of the coating composition into two or more sections so that the oxidizing agent and the reducing agent can be spaced from each other as described above. As each of the oxidizing agent and the reducing agent, any of the aforementioned oxidizing agents and reducing agents to be included in the primer composition as arbitrary components can be used.

One of these oxidizing agents or these reducing agents may be singly used, or two or more of them may be used together if necessary. The mixing ratio of each of the oxidizing agent and the reducing agent is preferably 0.01 wt % through 10 wt %, more preferably 0.05 wt % through 7 wt % and most preferably 0.1 wt % through 5 wt % based on the total weight of the polymeric monomer(s) included in the coating composition.

The coating composition may include an inorganic filler with a refractive index of 1.9 or more. The refractive index herein means a refractive index measured with light of a wavelength of 589.3 nm at 20° C. The inorganic filler with a refractive index of 1.9 or more is very useful not only in improving the surface curing property of the coating layer by reducing the thickness of a surface unpolymerized layer formed after polymerically curing the composition but also in improving the aesthetic property because it increases opaque property against color-changed teeth and increases the brightness of the coating layer. From the viewpoint of the surface curing property and the improvement of the aesthetic property, an inorganic filler with a refractive index of 2.1 or more is preferably used. When the refractive index is lower than 1.9, the surface curing property may be lowered. Examples of the inorganic filler with a refractive index of 1.9 or more are titanium oxide (with a refractive index of 2.49 through 2.90), zirconium oxide (with a refractive index of 2.13 through 2.19) and zinc oxide (with a refractive index of 2.00 through 2.02). Also, the inorganic filler with a refractive index of 1.9 or more has an average particle diameter of preferably 0.1 Ξm through 100 μm and more preferably 0.1 μm through 80 μm. Although the reason why the surface unpolymerized layer formed after polymerically curing the composition is reduced in the thickness is not clearly found but the present inventors presume the reason as follows:

In general, when a polymeric monomer is polymerized by using a photopolymerization initiator, oxygen present in the air works as a polymerization inhibitor, and as a result, an unpolymerized layer with a thickness in micron unit is formed in a surface portion of the coating layer in contact with the air. When the coating layer includes a small amount of opaque inorganic filler (corresponding to a pigment) with a refractive index of 1.9 or more, the inorganic filler causes diffuse reflection of light (light emitted in starting the polymerization) entering the coating layer, and owing to the scattering effect of the light, the polymerizing property in the surface portion is improved. As a result, the unpolymerized layer formed in the surface portion after the polymerically curing the composition has a small thickness.

One of inorganic fillers with a refractive index of 1.9 or more may be singly used, or two or more of them may be used together if necessary. The mixing ratio of the inorganic filler with a refractive index of 1.9 or more is preferably 0.1 wt % through 50 wt % based on the total weight of the coating composition. When the mixing ratio is smaller than 0.1 wt %, the surface curing property tends to be lowered, and when the mixing ratio exceeds 50 wt %, the curing depth attained by a photopolymerization catalyst alone tends to be too small to sufficiently cure the inside portion of the layer. The mixing ratio is more preferably 0.1 wt % through 10 wt % and most preferably 0.1 wt % through 5 wt %.

In order to suppress precipitation of the inorganic filler with a refractive index of 1.9 or more or to improve the mechanical strength, the coating property, easiness in taking out of a vessel and the operability, another filler may be used together. Examples of the filler to be used together with the inorganic filler with a refractive index of 1.9 or more are an inorganic filler, an organic filler and an organo-mineral composite filler all having a refractive index less than 1.9. As the inorganic filler, the organic filler and the organo-mineral composite filler, any of the aforementioned inorganic fillers, organic fillers and organo-mineral fillers to be included in the primer composition as an arbitrary component can be used.

As the filler to be used together with the inorganic filler with a refractive index of 1.9 or more, one of the aforementioned fillers may be singly used, or two or more of them may be used together if necessary. The mixing ratio of the filler to be used together with the inorganic filler with a refractive index of 1.9 or more is preferably 60 wt % or less and more preferably 40 wt % or less based on the total weight of the coating composition. The filler to be used together with the inorganic filler with a refractive index of 1.9 or more preferably has an average particle diameter of 0.001 μm through 50 μm. In order to suppress the precipitation of the filler with a refractive index of 1.9 or more and to improve the coating property and the operability, colloidal silica with an average particle diameter of 0.001 μm through 0.1 μm is used in a ratio of preferably 1 wt % through 40 wt %, more preferably 3 wt % through 35 wt % and most preferably 5 wt % through 30 wt % based on the total weight of the coating composition. Examples of such colloidal silica are silica with a small particle diameter obtained by spray pyrolysis (for example, one manufactured by Japan Aerosil, trade name "Aerosil"), silica sol obtained by a wet method and monodisperse silica obtained by a sol-gel process.

The inorganic filler with a refractive index of 1.9 or more and the filler to be used together may be previously subjected to the coupling with a known coupling agent such as a silane coupling agent in order to improve the mechanical strength, the coating property, the operability and the flowability of the coating composition. As the coupling agent, any of the aforementioned coupling agents used for the filler to be included in the primer composition as an arbitrary component can be used.

The coating composition may include a pigment. When a pigment is included, the color tone of the resultant coating layer can be adjusted. Examples of the pigment are blood red, phthalocyanine blue and various azo pigments. One of these pigments may be singly used, or two or more of them may be used together if necessary. The mixing ratio of the pigment is not particularly specified, and the pigment is appropriately included in consideration of the color tone of the coating composition and the aesthetic property.

The coating composition may include a fluorine ion emitting substance. When the fluorine ion emitting substance is included, acid resistance can be given to the surfaces of the teeth. Examples of the fluorine ion emitting substance are fluorine glass such as fluoroaminosilicate glass, metal fluoride such as sodium fluoride, potassium fluoride, sodium monofluorophosphate, lithium fluoride or ytterbium fluoride, a fluorine ion emitting polymer such as a copolymer of methyl methacrylate and methacrylic fluoride disclosed in Japanese Laid-Open Patent Publication No. 5-85912 and cetylamine hydrofluoride.

The coating composition may include a polymerization inhibitor, a fluorescent agent and a ultraviolet absorbing agent. Also, in order to provide antibacterial activity, an antibacterial substance such as cetyl pyridinium chloride, benzalkonium chloride, (meth)acryloyloxydodecyl pyridinium bromide, (meth)acryloyloxyhexadecyl pyridinium chloride, (meth)acryloyloxydecyl ammonium chloride or 2-4-4'-trichloro-2'-hydroxydiphenyl ether may be included.

In the preparation of the coating composition, the respective components are preferably appropriately selected so as to attain appropriate viscosity. From the viewpoint of the coating property on teeth and the operability, the viscosity of the coating composition at 30° C. is preferably 300 cP through 50,000 cP, more preferably 500 cP through 30,000 cP and most preferably 1,000 cP through 20,000 cP. When the viscosity is lower than 300 cP, the flowability is so high that the operability may be lowered, and when it exceeds 50,000 cP, the coating property may be lowered so as to degrade uniformity in the color tone of the coating layer.

Next, a method for using the second kit, namely, a coating method using the second kit, will be described.

First, the primer composition is applied on the surfaces of teeth, and the applied primer composition is dried by using a dental air syringe if necessary until the primer composition loses its flowability, or in the case where the primer composition includes a polymerization initiator (a photopolymerization initiator and/or a chemical polymerization initiator), the thus coated layer is polymerically cured. Thus, a primer layer is formed (step 1).

Next, the coating composition is applied on the primer layer, and the thus coated layer is polymerically cured through light irradiation, so as to form an intermediate layer (step 2). In the case where the primer composition includes a photopolymerization initiator, the primer composition and the coating composition may be simultaneously polymerically cured through the light irradiation.

Ultimately, the surface smoothing composition is applied on the intermediate layer, and the thus coated layer is polymerically cured through light irradiation, so as to form a surface layer. Thus, a coating layer with a three-layered structure is formed on the teeth (step 3).

If a large amount of unpolymerized layer is present in a surface portion of the intermediate layer after step 2, the surface curing property of the surface layer obtained after step 3 may be insufficient. In order to prevent this, the unpolymerized layer is preferably wiped out with, for example, a sponge or the like after step 2.

The thickness of the coating composition applied in step 2 is preferably 0.005 mm through 1 mm, more preferably 0.01 mm through 0.7 mm and most preferably 0.1 mm through 0.5 mm.

When the layer of the applied coating composition is polymerically cured through the light irradiation, a light source of a xenone lamp, a halogen lamp, a mercury lamp, a light emitting diode or the like is suitably used. The time of the light irradiation depends upon the wavelength or the amount of the light. When a dental irradiator is used, the composition can be cured in approximately 3 seconds through 3 minutes.

Also the second kit is applicable not only to teeth not bleached but also to bleached teeth similarly to the first kit. The bleaching of teeth is recently spreading as means for making teeth white, and it is known that the surfaces of teeth are roughened by the bleaching. The second kit is also suitably used for such roughened teeth similarly to the first kit, so as to complement the effect of the bleaching and prevent the phenomenon of the color return otherwise occurring after the bleaching.

The second kit can be also used not only on teeth but also on a restorative dental material such as a metal, porcelain, ceramics or a composite curing substance similarly to the first kit.

Also, the second kit may be used in combination with a commercially available dental metal primer, a primer for adhering porcelain or a tooth plane cleaning agent such as a sodium hypochlorite solution similarly to the first kit.

EMBODIMENTS

The present invention will now be described in detail on the basis of preferred embodiments thereof, and it is noted that the invention is not limited to the following embodiments.

First, embodiments of the first kit will be described, and in Embodiments 1 through 12 (the embodiments of the first kit) and Comparative Examples 1 through 4 described below, teeth were all bleached by the following method:

[Bleaching Method for Teeth]

A gel bleaching agent was prepared by adding 3.5 ml of 35% hydrogen peroxide to one package of a bleaching agent (manufactured by Kerativ, trade name "Power Gel") and sufficiently mixing the resultant. This gel bleaching agent was applied, in a thickness of approximately 1 mm, on the labial surface of an extracted human central incisor, which was previously cleaned with a brush (manufactured by Nihon Shika Kogyosha Co., Ltd., trade name "brush-corn"). The labial surface of the central incisor coated with the gel bleaching agent was irradiated with light for 30 seconds by using a dental visible light irradiator (manufactured by AIR TECHNIQUES, trade name "Arc Light") and was allowed to stand for 5 minutes, and then, the labial surface of the central incisor was cleaned with running water. This operation from the application of the gel bleaching agent to the cleaning with running water was repeated by three times, and the bleaching was completed.

Abbreviations used in description below stand for the following:

[Acidic group-containing polymeric monomer (a)]
MDP: 10-(meth)acryloyloxydecyl dihydrogenphosphate
[Water-soluble solvent (c)]
HEMA: 2-hydroxyethyl methacrylate
[Polyfunctional polymeric monomer (f)]
DPHA: dipentaerythritol hexaacrylate
DPPA: dipentaerythritol pentaacrylate
PTA: pentaerythritol triacrylate
[Volatile solvent (g)]
MMA: methyl methacrylate
[Photopolymerization initiator (h)]
TMDPO: 2,4,6-trimethylbenzoyl diphenylphosphine oxide
CQ: camphorquinone
[Polymerization promoter]
DMABE: 4-dimethylaminobenzoate
[Phosphoric ester adhesive monomer]
PMEAP: phenyl(2-methacryloxyethyl) acid phosphate
DPMEP: diphenyl(methacryloxyethyl) phosphate Embodiment 1

A primer composition composed of MDP (20 wt %), distilled water (25 wt %) and HEMA (55 wt %) was prepared. Also, a surface smoothing composition composed of DPHA (93 wt %), MMA (5 wt %) and TMDPO (2 wt %) was prepared. With respect to a coating kit including the primer composition and the surface smoothing composition, the viscosity of the surface smoothing composition was obtained by a method described in a paragraph (1) below. Also, the operability, the odor and the surface curing property were checked by methods described in paragraphs (2) through (4) below. The results are shown in Table 1. It is noted that the viscosity, the operability, the odor and the surface curing property obtained in embodiments and comparative examples described below were also obtained by the methods of the paragraphs (1) through (4).

(1) Viscosity

The viscosity at 30° C. of 0.6 cc of the surface smoothing composition collected from the kit was measured with a cornplate-type viscometer (manufactured by Toki Sangyo Co., Ltd.).

(2) Operability

The primer composition prepared in Embodiment 1 was applied on a bleached human central incisor, the resultant was allowed to stand for 30 seconds, and a volatile component was perspired with a dental air syringe until the primer composition lost its flowability. Subsequently, the central incisor was fixed in parallel to the ground with the labial surface thereof facing upward, and the surface smoothing composition prepared in Embodiment 1 was applied on the labial surface from the cutting edge to the cervical line with a small brush. Thus, run of the composition to a space between adjacent teeth or to a radicular surface and pool of the composition in the vicinity of the cutting edge were visually evaluated. A kit in which neither run nor pool was found was evaluated as ◯, a kit in which the run and the pool were slightly found was evaluated as Δ, and a kit in which they were conspicuously found was evaluated as ×.

(3) Odor

The surface coated with the surface smoothing composition in the paragraph (2) was irradiated with light for 60 seconds by using a dental irradiator (manufactured by Gunma Ushio Electric Inc., trade code "LIGHTEL II"), so as to cure the surface smoothing composition. At the time of curing, the nostril of a panelist was fixed in a position 3 cm above the coated surface so as to evaluate the odor of the surface smoothing composition. Seven panelists were employed, a panelist that did not feel the odor gave 3 marks, a panelist that felt the odor but was not uncomfortable gave 2 marks, and a panelist that felt the odor uncomfortable gave 1 mark. A kit in which the average marks of the seven panelists were 2 marks or more was evaluated as ○ and a kit in which the average marks were less than 2 marks was evaluated as ×.

(4) Surface Curing Property

The surface of the cured surface layer obtained in the paragraph (3) was strongly scraped with a wiper (manufactured by Crecia Corporation, trade code "JK wiper"), so as to visually evaluate the surface curing property. A kit in which the surface layer was sufficiently cured with no flaw found on the surface was evaluated as ○ and a kit in which the surface layer was insufficiently cured with flaws found on the surface was evaluated as ×.

Embodiments 2 through 7

Six kinds of surface smoothing compositions were prepared by mixing DPHA, DPPA, PTA, MMA, ethanol, TMDPO, CQ and DMABE in weight ratios listed in Table 1. With respect to coating kits each including each of these surface smoothing compositions and the primer composition prepared in Embodiment 1, the viscosity of the surface smoothing composition was obtained and the operability, the odor and the surface curing property were checked. The results are shown in Table 1.

TABLE 1

| | | Mixing ratios in each composition (wt %) | | | | | | |
|---|---|---|---|---|---|---|---|---|
| | | Emb. 1 | Emb. 2 | Emb. 3 | Emb. 4 | Emb. 5 | Emb. 6 | Emb. 7 |
| Primer composition | Acidic group-containing polymeric monomer (a): | | | | | | | |
| | MDP | 20 | 20 | 20 | 20 | 20 | 20 | 20 |
| | Water (b): | | | | | | | |
| | Distilled water | 25 | 25 | 25 | 25 | 25 | 25 | 25 |
| | Water-soluble solvent (c): | | | | | | | |
| | HEMA | 55 | 55 | 55 | 55 | 55 | 55 | 55 |
| Surface smoothing composition | Polyfunctional polymeric monomer (f): | | | | | | | |
| | DPHA | 93 | 88 | 88 | 88 | — | — | 83 |
| | DPPA | — | — | — | — | 88 | — | — |
| | PTA | — | — | — | — | — | 88 | — |
| | Volatile solvent (g): | | | | | | | |
| | MMA | 5 | 10 | 10 | — | 10 | 10 | 15 |
| | Ethanol | — | — | — | 10 | — | — | — |
| | Photopolymerization initiator (h): | | | | | | | |
| | TMDPO | 2 | 2 | — | 2 | 2 | 2 | 2 |
| | CQ | — | — | 2 | — | — | — | — |
| | Polymerization promoter: | | | | | | | |
| | DMABE | — | — | 2 | — | — | — | — |
| Viscosity of surface smoothing composition (cP) | | 310 | 205 | 204 | 198 | 201 | 185 | 124 |
| Operability | | ○ | ○ | ○ | ○ | ○ | ○ | ○ |
| Odor | | ○ | ○ | ○ | ○ | ○ | ○ | ○ |
| Surface curing property | | ○ | ○ | ○ | ○ | ○ | ○ | ○ |

It is understood from Table 1 that the first kits according to Embodiments 1 through 7 emit less uncomfortable odor and are good at operability. Also, since the first kits according to Embodiments 1 through 7 do not include a phosphoric ester adhesive monomer in the surface smoothing compositions, they are good at surface curing property.

Embodiment 8

A primer composition including MDP (10 wt %), distilled water (30 wt %) and HEMA (60 wt %) was prepared. A coating kit including this primer composition and the surface smoothing composition prepared in Embodiment 1 was used for forming a surface layer by a method described in a paragraph (1) below, and the surface curing property thereof was evaluated. Also, the adhesive strength to a bleached tooth of the surface layer was obtained by a method described in a paragraph (2) below. The adhesive strengths obtained in Embodiments 9 through 12 and Comparative Examples 1 through 4 below were also obtained by the method described below. The results are shown in Table 2.

(1) Formation of Surface Layer

A tape with a thickness of 150 μm having a hole with a diameter of 3 mm was adhered on the center of a bleached human central incisor, and the primer composition prepared in Embodiment 8 was applied on the inside of the hole of the tape. After allowing it to stand for 30 seconds, a volatile component was perspired with a dental air syringe until the primer composition lost its flowability, so as to form a primer layer. Subsequently, the surface smoothing composition prepared in Embodiment 1 was applied on the primer layer so as to fill the hole. The thus coated surface was irradiated with a dental irradiator (manufactured by Gunma Ushio Electric Inc., trade code "LIGHTEL II") for 60 seconds for polymerically curing the composition, so as to form a surface layer.

(2) Adhesive Strength

A stainless steel cylindrical bar (with a diameter of 5mm and a length of 1.5 cm) was adhered to the surface layer with an end face (circular face) of the bar used as an adhesive surface by using a commercially available resin cement (manufactured by Kuraray Co., Ltd., trade code "Panavia 21"). After thirty minutes, the thus obtained test piece was immersed in water at 37° C., and the adhesive strength was measured one day after. The adhesive strength was measured by pulling the stainless steel bar downward with the tooth fixed by using several metal plates each with a thickness of 0.5 mm so that the stainless steel cylindrical bar extend within a range of ±5° or less against the axis of the pulling direction. The adhesive strength was measured by using a tensile testing apparatus (manufactured by Shimadzu Corporation, trade name "Autograph") with a cross head speed set to 2 mm/min. The adhesive strength was obtained as an average value of values measured in eight test pieces.

Embodiments 9 through 12

Four kinds of primer compositions were prepared by mixing MDP, distilled water, HEMA, ethanol, CQ and DMABE in weight ratios listed in Table 2. With respect to coating kits each including each of these primer compositions and the surface smoothing composition prepared in Embodiment 1, the surface curing property of the surface layer was evaluated. Also, the adhesive strength to a bleached tooth was obtained. The results are shown in Table 2.

COMPARATIVE EXAMPLE 1

A tape with a thickness of 150 μm having a hole with a diameter of 3 mm was adhered on the center of a bleached human central incisor, and the surface smoothing composition prepared in Embodiment 1 was applied on the inside of the hole of the tape. With the surface smoothing composition filled in the hole of the tape, the thus coated surface was irradiated with a dental irradiator (manufactured by Gunma Ushio Electric Inc., trade code "LIGHTEL II") for 60 seconds so as to form a coating layer on the bleached tooth. With respect to this coating layer, the surface curing property was evaluated and the adhesive strength to the bleached tooth was obtained. The results are shown in Table 2.

COMPARATIVE EXAMPLES 2 THROUGH 4

Four kinds of surface smoothing compositions were prepared by mixing DPHA, MMA, CQ, DMABE and a phosphoric ester adhesive monomer (phenyl(2-methacryloylethy) acid phosphate or diphenyl(methacryloxyethyl) phosphate) in weight ratios listed in Table 2. Each of these surface smoothing compositions was directly applied on the labial surface of a bleached human central incisor so as to form a coating layer. With respect to this coating layer, the surface curing property was evaluated and the adhesive strength to the bleached tooth was obtained. The results are shown in Table 2.

TABLE 2

| | | Mixing ratios in each composition (wt %) | | | | | | | | |
|---|---|---|---|---|---|---|---|---|---|---|
| | | Emb. 8 | Emb. 9 | Emb. 10 | Emb. 11 | Emb. 12 | Com. Ex. 1 | Com. Ex. 2 | Com. Ex. 3 | Com. Ex. 4 |
| Primer composition | Acidic group-containing polymeric monomer (a): | | | | | | | | | |
| | MDP | 10 | 30 | 50 | 20 | 20 | — | — | — | — |
| | Water (b): | | | | | | | | | |
| | Distilled water | 30 | 20 | 15 | 25 | 25 | — | — | — | — |
| | Water-soluble solvent (c): | | | | | | | | | |
| | HEMA | 60 | 50 | 35 | — | 53 | — | — | — | — |
| | Ethanol | — | — | — | 55 | — | — | — | — | — |
| | Photo-polymerization initiator: | | | | | | | | | |
| | CQ | — | — | — | — | 1 | — | — | — | — |
| | Polymerization promoter: | | | | | | | | | |
| | DMABE | — | — | — | — | 1 | — | — | — | — |

TABLE 2-continued

| | | \multicolumn{9}{c|}{Mixing ratios in each composition (wt %)} |
|---|---|---|---|---|---|---|---|---|---|---|
| | | Emb. 8 | Emb. 9 | Emb. 10 | Emb. 11 | Emb. 12 | Com. Ex. 1 | Com. Ex. 2 | Com. Ex. 3 | Com. Ex. 4 |
| Surface smoothing composition | Polyfunctional polymeric monomer (f): | | | | | | | | | |
| | DPHA | 88 | 88 | 88 | 88 | 88 | 88 | 56 | 54 | 54 |
| | Volatile solvent (g): | | | | | | | | | |
| | MMA | 10 | 10 | 10 | 10 | 10 | 10 | 40 | 40 | 40 |
| | Photo-polymerization initiator (h): | | | | | | | | | |
| | TMDPO | 2 | 2 | 2 | 2 | 2 | 2 | — | — | — |
| | CQ | — | — | — | — | — | — | 2 | 2 | 2 |
| | Polymerization promoter: | | | | | | | | | |
| | DMABE | — | — | — | — | — | — | 2 | 2 | 2 |
| | Phosphoric ester adhesive monomer: | | | | | | | | | |
| | PMEAP | — | — | — | — | — | — | — | 2 | — |
| | DPMEP | — | — | — | — | — | — | — | — | 2 |
| Surface curing property | | ○ | ○ | ○ | ○ | ○ | ○ | ○ | X | X |
| Adhesive strength (MPa) | | 15.3 | 14.8 | 15.6 | 15.2 | 15.9 | 1.5 | 1.3 | 3.7 | 3.9 |

It is understood from Table 2 that very high adhesive strength can be obtained when a primer layer and a surface layer are successively formed on a bleached tooth by using the first kit according to any of Embodiments 8 through 12. Also, since the first kit of any of Embodiments 8 through 12 does not include a phosphoric ester adhesive monomer in its surface smoothing composition, it is good at the surface curing property. On the contrary, in the case where a surface smoothing composition is directly applied on a bleached tooth without forming a primer layer (Comparative Examples 1 and 2), although the surface curing property is high, the adhesive strength is very low. Alternatively, in the case where a composition including a phosphoric ester adhesive monomer is directly applied on a bleached tooth without forming a primer layer, although the adhesiveness to the bleached tooth is slightly improved, the surface curing property is poor (Comparative Examples 3 and 4).

Although the first kit is used for coating a bleached tooth in each of the aforementioned embodiments, the first kit is suitably used for a tooth not having been bleached.

Next, preferred embodiments of the second kit will be described. Abbreviations used in description below stand for the following:

MDP: 10-(meth)acryloyloxydecyl dihydrogenphosphate
HEMA: 2-hydroxyethyl methacrylate
UDMA: [2,2,4-trimethylhexamethylenebis(2-carbamoyloxyethyl)]dimethacrylate
U-4TH: N,N'-(2,2,4-trimethylhexamethylene)bis[2-(aminocarboxy)propane-1,3-diol]tetramethacrylate
Bis-GMA: bisphenol A diglycidyl methacrylate
3G: triethylene glycol dimethacrylate
DPHA: dipentaerythritol hexaacrylate
DPPA: dipentaerythritol pentaacrylate
MMA: methyl methacrylate
CQ: camphorquionone
DMABE: 4-dimethylaminobenzoate
TMDPO: 2,4,6-trimethylbenzoyl diphenylphosphine oxide Embodiment 13

A primer composition including MDP (20 wt %), distilled water (40 wt %) and HEMA (40 wt %), a coating composition including UDMA (50 wt %), U-4TH (20 wt %), 3G (29 wt %), CQ (0.5 wt %) and DMABE (0.5 wt %) and a surface smoothing composition including DPHA (73 wt %), MMA (25 wt %) and TMDPO (2 wt %) were respectively prepared. With respect to a coating kit (second kit) including these primer composition, coating composition and surface smoothing composition, the adhesive strength to a tooth was measured by an adhesiveness testing method A1 described below. Also, the chipping resistance was evaluated by a chipping resistance testing method B1 described below. The results are shown in Table 3.

[Adhesiveness Testing Method A1]

(1) After cleaning the enamel surface on the labial surface of an extracted human central incisor with a brush (manufactured by Nihon Shika Kogyo Co., Ltd., trade name "brushcorn"), a tape with a thickness of 150 μm having a hole with a diameter of 3 mm was adhered to the center of a flat portion of the enamel surface, and the primer composition prepared in Embodiment 13 was applied on the inside of the hole of the tape. After allowing it to stand for 30 seconds, a volatile component was perspired with a dental air syringe until the primer composition lost its flowability, so as to form a primer layer. The coating composition prepared in Embodiment 13 was applied on the primer layer so as to fill the hole. The thus coated surface was irradiated with a dental irradiator (manufactured by Gunma Ushio Electric Inc., trade code "LIGHTEL II") for 30 seconds for curing, so as to form an intermediate layer. Furthermore, the surface smoothing composition prepared in Embodiment 13 was applied on the intermediate layer with a small brush, and the resultant was irradiated with the aforementioned dental irradiator for 60 seconds, so as to form a surface layer.

(2) A stainless steel cylindrical bar (with a diameter of 5mm and a length of 1.5 cm) was adhered to the surface layer with an end face (circular face) of the bar used as an adhesive surface by using a commercially available resin cement (manufactured by Kuraray Co., Ltd., trade code "Panavia 21"). After thirty minutes, the thus obtained test piece was immersed in water at 37° C., and the adhesive strength was measured one day after. The adhesive strength was measured by pulling the stainless steel bar downward with the tooth fixed by using several metal plates each with a thickness of 0.5 mm so that the stainless steel cylindrical bar extend within a range of ±5° or less against the axis of the pulling direction. The adhesive strength was measured by using a tensile testing apparatus (manufactured by Shimadzu Corporation, trade name "Autograph") with a cross head speed set to 2 mm/min. The adhesive strength was obtained as an average value of values measured in eight test pieces.

[Chipping resistance testing method B1]

(1) The lingual surface of an extracted human anterior tooth was planed off to be parallel to a flat portion of the enamel surface on the labial surface, and thus, the tooth was processed into a tabular shape with a thickness of 2 mm. After cleaning the enamel surface on the labial surface of the thus processed tooth with a brush (manufactured by Nihon Shika Kogyo Co., Ltd., trade name "brush-corn"), a tape with a thickness of 150 μm having a hole with a diameter of 5 mm was adhered to the center of the flat portion of the enamel surface, and the primer composition prepared in Embodiment 13 was applied. After allowing it to stand for 30 seconds, a volatile component was perspired with a dental air syringe until the primer composition lost its flowability, so as to form a primer layer. The coating composition prepared in Embodiment 13 was applied on the primer layer so as to fill the hole. The thus coated surface was irradiated with a dental irradiator (manufactured by Gunma Ushio Electric Inc., trade code "LIGHTEL II") for 30 seconds for curing, so as to form an intermediate layer. Furthermore, the surface smoothing composition prepared in Embodiment 13 was applied on the intermediate layer with a small brush, and the resultant was irradiated with the aforementioned dental irradiator for 60 seconds. Thereafter, the tape was peeled off, resulting in obtaining a tabular tooth having a surface layer with a diameter of 5 mm formed on the enamel surface. The tabular tooth having the surface layer was placed on the center of a mold with a length of 3 cm, a width of 2 cm and a thickness of 2 mm with the circular surface layer facing upward, the tooth was fixed by filling the periphery with a dental composite resin, and in this state, the dental composite resin was polymerically cured, so as to obtain a test piece. The test piece was fixed on the bottom of a water bath filled with water, the brush tip of a toothbrush (manufactured by Lion Corporation, trade name "Between"; hardness: medium) was vertically brought to contact with the surface of the surface layer, and the toothbrush was reciprocated by a swing range of 10 cm under a load of 250 g. (2) After repeating the reciprocation by 10000 times, 20000 times and 40000 times, the test piece was taken out, the peripheral portion of the circular surface layer was observed with a light microscope (of 10 magnifications). Thus, occurrence of chipping with a major axis of 0.1 mm or more was checked, and the chipping resistance was evaluated in accordance with the following evaluation criterion:

(Evaluation Criterion)

No chipping was found: ○

Any chipping was found: ×

Embodiments 14 through 17

Four kinds of dental coating kits (second kits) were fabricated by preparing primer compositions, coating compositions and surface smoothing compositions respectively having compositions listed in Table 3. With respect to each of these dental coating kits, the adhesive strength was obtained by the aforementioned adhesiveness testing method A1 and the chipping resistance was evaluated by the aforementioned chipping resistance testing method B1. The results are shown in Table 3.

COMPARATIVE EXAMPLES 5 AND 6

With respect to each of the surface smoothing composition prepared in Embodiment 13 (as Comparative Example 5) and the surface smoothing composition prepared in Comparative Example 1 (as Comparative Example 6), the adhesive strength was obtained by an adhesiveness testing method A2 described below and the chipping resistance was evaluated by a chipping resistance testing method B2 described below. The results are shown in Table 3. However, although a test piece was to be taken out for evaluating the chipping resistance after 10000 reciprocations, the coating layers of both Comparative Example 5 and Comparative Example 6 were dropped off from the teeth before the 10000 reciprocations for the chipping resistance test, and therefore, the chipping resistance could not be evaluated.

[Adhesiveness Testing Method A2]

(1) After cleaning the enamel surface on the labial surface of an extracted human central incisor with a brush (manufactured by Nihon Shika Kogyo Co., Ltd., trade name "brush-corn"), a tape with a thickness of 150 μm having a hole with a diameter of 3 mm was adhered to the center of a flat portion of the enamel surface, and the surface smoothing composition prepared in Embodiment 13 or Comparative Example 1 was applied on the inside of the hole of the tape. The thus coated surface was irradiated with a dental irradiator (manufactured by Gunma Ushio Electric Inc., trade code "LIGHTEL II") for 60 seconds for curing, so as to form a coating layer. (2) The adhesive strength to the tooth of the coating layer formed by the method described in the paragraph (1) was measured by the aforementioned adhesiveness testing method A1 (2).

[Chipping resistance testing method B2]

(1) The lingual surface of an extracted human anterior tooth was planed off to be parallel to a flat portion of the enamel surface on the labial surface, and thus, the tooth was processed into a tabular shape with a thickness of 2 mm. After cleaning the enamel surface on the labial surface of the thus processed tooth with a brush (manufactured by Nihon Shika Kogyo Co., Ltd., trade name "brush-corn"), a tape with a thickness of 150 μm having a hole with a diameter of 5 mm was adhered to the center of the flat portion of the enamel surface, and the surface smoothing composition prepared in Embodiment 13 or Comparative Example 1 was applied. The thus coated surface was irradiated with the aforementioned dental irradiator for 60 seconds for curing, and the tape was peeled off, resulting in obtaining a tabular tooth having a coating layer with a diameter of 5 mm formed on the enamel surface. (2) The chipping resistance of the coating layer formed in the method described in the paragraph (1) was evaluated by the chipping resistance testing method B1 (2).

TABLE 3

| | | Mixing ratios in each composition (wt %) | | | | | | |
|---|---|---|---|---|---|---|---|---|
| | | Emb. 13 | Emb. 14 | Emb. 15 | Emb. 16 | Emb. 17 | Com. Ex. 5 | Com. Ex. 6 |
| Primer composition | Acidic group-containing polymeric monomer (a): | | | | | | | |
| | MDP | 20 | 20 | 20 | 20 | 20 | — | — |
| | Water (b): | | | | | | | |
| | Distilled water | 40 | 40 | 40 | 40 | 40 | — | — |
| | Water-soluble solvent (c): | | | | | | | |
| | HEMA | 40 | — | 40 | 40 | 40 | — | — |
| | Ethanol | — | 40 | — | — | — | — | — |
| Coating composition | Polymeric monomer (d): | | | | | | | |
| | UDMA | 50 | 50 | — | 50 | — | — | — |
| | U-4TH | 20 | 20 | — | 20 | — | — | — |
| | Bis-GMA | — | — | 60 | — | 60 | — | — |
| | 3G | 29 | 29 | 39 | — | — | — | — |
| | HEMA | — | — | — | 29 | 39 | — | — |
| | Photo-polymerization initiator (e): | | | | | | | |
| | CQ | 0.5 | 0.5 | 0.5 | 0.5 | 0.5 | — | — |
| | Polymerization promoter: | | | | | | | |
| | DMABE | 0.5 | 0.5 | 0.5 | 0.5 | 0.5 | — | — |
| Surface smoothing composition | Polyfunctional polymeric monomer (f): | | | | | | | |
| | DPHA | 73 | 73 | 73 | 73 | 73 | 73 | 88 |
| | Volatile solvent (g): | | | | | | | |
| | MMA | 25 | 25 | 25 | 25 | 25 | 25 | 10 |
| | Photo-polymerization initiator (h): | | | | | | | |
| | TMDPO | 2 | 2 | 2 | 2 | 2 | 2 | 2 |
| Adhesive strength (MPa) | | 15.4 | 14.6 | 14.7 | 15.7 | 15.5 | 0.3 | 1.5 |
| Chipping resistance | 10000 reciprocations | ○ | ○ | ○ | ○ | ○ | — | — |
| | 20000 reciprocations | ○ | ○ | ○ | ○ | ○ | — | — |
| | 40000 reciprocations | ○ | ○ | ○ | ○ | ○ | — | — |

Embodiments 18 through 22

Five kinds of dental coating kits (second kits) were fabricated by preparing primer compositions, coating compositions and surface smoothing compositions respectively having compositions listed in Table 4. With respect to each of these dental coating kits, the adhesive strength was obtained by the aforementioned adhesiveness testing method A1 and the chipping resistance was evaluated by the aforementioned chipping resistance testing method B1. The results are shown in Table 4.

TABLE 4

| | | Mixing ratios in each composition (wt %) | | | | |
|---|---|---|---|---|---|---|
| | | Emb. 18 | Emb. 19 | Emb. 20 | Emb. 21 | Emb. 22 |
| Primer composition | Acidic group-containing polymeric monomer (a): | | | | | |
| | MDP | 20 | 20 | 20 | 20 | 20 |

TABLE 4-continued

| | | Mixing ratios in each composition (wt %) | | | | |
|---|---|---|---|---|---|---|
| | | Emb. 18 | Emb. 19 | Emb. 20 | Emb. 21 | Emb. 22 |
| | Water (b): | | | | | |
| | Distilled water | 40 | 40 | 40 | 40 | 40 |
| | Water-soluble solvent (c): | | | | | |
| Coating composition | HEMA | 40 | 40 | 40 | 40 | 40 |
| | Polymeric monomer (d): | | | | | |
| | UDMA | 50 | 50 | 50 | 50 | 50 |
| | U-4TH | 20 | 20 | 20 | 20 | 20 |
| | 3G | 29 | 29 | 29 | 29 | 29 |
| | Photopolymerization initiator (e): | | | | | |
| | CQ | 0.5 | 0.5 | 0.5 | 0.5 | 0.5 |
| | Polymerization promoter: | | | | | |
| | DMABE | 0.5 | 0.5 | 0.5 | 0.5 | 0.5 |
| Surface smoothing composition | Polyfunctional polymeric monomer (f): | | | | | |
| | DPHA | 83 | — | 73 | 85 | 70 |
| | DPPA | — | 73 | — | — | — |
| | Volatile solvent (g): | | | | | |
| | MMA | 15 | 25 | — | 10 | 25 |
| | Ethanol | | | 25 | | |
| | Photopolymerization initiator (h): | | | | | |
| | TMDPO | 2 | 2 | 2 | — | — |
| | CQ | — | — | — | 2.5 | 2.5 |
| | Polymerization promoter: | | | | | |
| | DMABE | — | — | — | 2.5 | 2.5 |
| Adhesive strength (MPa) | | 15.6 | 14.9 | 15.3 | 15.8 | 14.6 |
| Chipping resistance | 10000 reciprocations | ○ | ○ | ○ | ○ | ○ |
| | 20000 reciprocations | ○ | ○ | ○ | ○ | ○ |
| | 40000 reciprocations | ○ | ○ | ○ | ○ | ○ |

Embodiments 23 through 37

Seven kinds of dental coating kits (according to Embodiments 23 through 29; second kits) were fabricated by preparing primer compositions, coating compositions and surface smoothing compositions respectively having compositions listed in Table 5. Also, eight kinds of dental coating kits (according to Embodiments 30 through 37; first kits) were fabricated by preparing primer compositions and surface smoothing compositions respectively having compositions listed in Table 6. The kit of Embodiment 32 is the same as the kit of Embodiment 7, the kit of Embodiment 33 is the same as the kit of Embodiment 2, the kit of Embodiment 34 is the same as the kit of Embodiment 1, the kit of Embodiment 35 is the same as the kit of Embodiment 8, the kit of Embodiment 36 is the same as the kit of Embodiment 9, and the kit of Embodiment 37 is the same as the kit of Embodiment 10. With each of these dental coating kits, the adhesive strength was obtained by the aforementioned adhesiveness testing method A1 and the chipping resistance was evaluated by the aforementioned chipping resistance testing method B1. Furthermore, change of the brightness of a tooth caused by the coating was measured by a measurement method for brightness change described below. The results are shown in Table 5 and Table 6.

[Measurement Method for Brightness Change]

(1) The lingual surface of an extracted human anterior tooth was planed off to be parallel to a flat portion of the enamel surface on the labial surface, and thus, the tooth was processed into a tabular shape with a thickness of 2 mm. After cleaning the enamel surface on the labial surface of the thus processed tooth with a brush (manufactured by Nihon Shika Kogyo Co., Ltd., trade name "brush-corn"), a tape with a thickness of 150 μm having a hole with a diameter of 7 mm was adhered to the center of the flat portion of the enamel surface, and the brightness index of the hole portion was measured ($L^*_0$). The brightness index ($L^*$) was measured by using a color difference meter (manufactured by Nippon Denshoku Industries Co., Ltd., Σ90 type, with a light source of a D65 light source, a view angle of 2 degrees and a color measuring range of 5 mmφ) with a standard white board placed behind. The $L^*$ described herein corresponds to a brightness index in a $L^*a^*b^*$ color system according to JIS-Z8729.

(2) Subsequently, the primer composition prepared in any of Embodiments 23 through 37 was applied on the inside of the hole of the tape. After allowing it to stand for 30 seconds, a volatile component was perspired with a dental air syringe until the flowability was lost, so as to form a primer layer.

(3) Subsequently, the coating composition prepared in any of Embodiments 23 through 29 was applied on the primer layer so as to fill the hole. The thus coated surface was irradiated with the aforementioned dental irradiator for 30 seconds for polymerically curing the composition, so as to form an intermediate layer. With respect to the kits of Embodiments 30 through 37 including no coating composition, this step (3) was omitted and the process proceeded to step (4) below.

(4) The surface smoothing composition prepared in any of Embodiments 23 through 37 was applied on the intermediate layer (on the primer layer in Embodiments 30 through 37) with a small brush, and the resultant was irradiated by using the aforementioned dental irradiator for 60 seconds, and then the tape was peeled off. Thus, a tabular tooth having a coating layer with a diameter of 7 mm on the enamel surface was obtained.

(5) Subsequently, the brightness index of the coating portion of the tabular tooth was measured in the same manner as in step (1) above ($L^*_1$). Change of the brightness caused by the coating was calculated in accordance with the following formula:

Change of brightness $(\Delta L^*) = L^*_1 - L^*_0$

TABLE 5

| | | Mixing ratios in each composition (wt %) | | | | | | |
|---|---|---|---|---|---|---|---|---|
| | | Emb. 23 | Emb. 24 | Emb. 25 | Emb. 26 | Emb. 27 | Emb. 28 | Emb. 29 |
| Primer composition | Acidic group-containing polymeric monomer (a): | | | | | | | |
| | MDP | 20 | 20 | 20 | 20 | 20 | 20 | 20 |
| | Water (b): | | | | | | | |
| | Distilled water | 40 | 40 | 40 | 40 | 40 | 40 | 40 |
| | Water-soluble solvent (c): | | | | | | | |
| | HEMA | 40 | 40 | 40 | 40 | 40 | 40 | 40 |
| Coating composition | Polymeric monomer (d): | | | | | | | |
| | UDMA | 50 | 50 | 50 | 50 | 80.9 | 65.9 | 50.9 |
| | U-4TH | 20 | 20 | 20 | 20 | — | — | — |
| | 3G | 21.3 | 20.9 | 20.5 | 18.5 | — | — | — |
| | HEMA | | | | | 10 | 25 | 40 |
| | Photo-polymerization initiator (e): | | | | | | | |
| | CQ | 0.5 | 0.5 | 0.5 | 0.5 | 0.5 | 0.5 | 0.5 |
| | Polymerization promoter: | | | | | | | |
| | DMABE | 0.5 | 0.5 | 0.5 | 0.5 | 0.5 | 0.5 | 0.5 |
| | Inorganic filler (i): | | | | | | | |
| | Titanium oxide powder (*1) | 0.2 | 0.6 | 1.0 | 3.0 | 0.6 | 0.6 | 0.6 |
| | Colloidal silica (j): | | | | | | | |
| | Aerosil 130 (*2) | 7.5 | 7.5 | 7.5 | 7.5 | 7.5 | 7.5 | 7.5 |
| Surface smoothing composition | Polyfunctional polymeric monomer (f): | | | | | | | |
| | DPHA | 73 | 73 | 73 | 73 | 83 | 83 | 83 |
| | Volatile solvent (g): | | | | | | | |
| | MMA | 25 | 25 | 25 | 25 | 15 | 15 | 15 |
| | Photo-polymerization initiator (h): | | | | | | | |
| | TMDPO | 2 | 2 | 2 | 2 | 2 | 2 | 2 |
| Adhesive strength (MPa) | | 16.0 | 15.1 | 15.7 | 14.9 | 18.5 | 17.8 | 18.2 |
| Chipping resistance | 10000 reciprocations | ○ | ○ | ○ | ○ | ○ | ○ | ○ |

TABLE 5-continued

| | | Mixing ratios in each composition (wt %) | | | | | | |
|---|---|---|---|---|---|---|---|---|
| | | Emb. 23 | Emb. 24 | Emb. 25 | Emb. 26 | Emb. 27 | Emb. 28 | Emb. 29 |
| | 20000 reciprocations | ○ | ○ | ○ | ○ | ○ | ○ | ○ |
| | 40000 reciprocations | ○ | ○ | ○ | ○ | ○ | ○ | ○ |
| Change of brightness ($\Delta L^*$) | | 8.1 | 17.1 | 19.5 | 22.5 | 17.4 | 17.3 | 17.0 |

(*1) titanium oxide powder having been subjected to silane treatment with γ-methacryloxypropyl trimethoxysilane
(*2) manufactured by Japan Aerosil (trade name)

TABLE 6

| | | Mixing ratios in each composition (wt %) | | | | | | | |
|---|---|---|---|---|---|---|---|---|---|
| | | Emb. 30 | Emb. 31 | Emb. 32 | Emb. 33 | Emb. 34 | Emb. 35 | Emb. 36 | Emb. 37 |
| Primer composition | Acetic group-containing polymeric monomer (a): | | | | | | | | |
| | MDP | 20 | 20 | 20 | 20 | 20 | 10 | 30 | 50 |
| | Water (b): | | | | | | | | |
| | Distilled water | 40 | 25 | 25 | 25 | 25 | 30 | 20 | 15 |
| | Water-soluble solvent (c): | | | | | | | | |
| | HEMA | 40 | 55 | 55 | 55 | 55 | 60 | 50 | 35 |
| Surface smoothing composition | Polyfunctional polymeric monomer (f): | | | | | | | | |
| | DPHA | 73 | 73 | 83 | 88 | 93 | 88 | 88 | 88 |
| | Volatile solvent (g): | | | | | | | | |
| | MMA | 25 | 25 | 15 | 10 | 5 | 10 | 10 | 10 |
| | Photopolymerization initiator (h): | | | | | | | | |
| | TMDPO | 2 | 2 | 2 | 2 | 2 | 2 | 2 | 2 |
| Adhesive strength (MPa) | | 11.2 | 12.5 | 13.7 | 14.2 | 13.9 | 15.3 | 14.8 | 15.6 |
| Chipping resistance | 10000 reciprocations | ○ | ○ | ○ | ○ | ○ | ○ | ○ | ○ |
| | 20000 reciprocations | ○ | ○ | ○ | ○ | ○ | ○ | ○ | ○ |
| | 40000 reciprocations | X | X | X | X | X | X | X | X |

As shown in Tables 3 through 5, in the case where a coating layer with a three-layered structure was formed by using a second kit including a primer composition, a coating composition and a surface smoothing composition, the resultant coating layer exhibited high adhesive strength to teeth, and in addition, was good at chipping resistance (Embodiments 13 through 29). On the contrary, as shown in Table 3, in the case where a single-layered coating layer was formed by directly applying a surface smoothing composition on a tooth without applying a primer composition and a coating composition, the adhesiveness to the tooth of the resultant coating layer was poor (Comparative Examples 5 and 6). Also, as shown in Table 6, in the case where a coating layer with a two-layered structure was formed by applying a primer composition and a surface smoothing composition in this order on a tooth without applying a coating composition, although the adhesive strength was high, the chipping resistance was poor (Embodiments 30 through 37).

Also, as shown in Table 5, in the case where a coating layer with a three-layered structure was formed on a tooth by using a second kit including a coating composition containing an inorganic filler with a refractive index of 1.9 or more, the brightness of the tooth was improved through the coating, and the aesthetic property was improved (Embodiments 23 through 29).

INDUSTRIAL APPLICABILITY

The dental coating kit according to this invention is particularly useful as a kit for preventing stain and color return of bleached teeth.

The invention claimed is:
1. A dental coating kit comprising:
a primer composition including at least one acidic group-containing monomer (a), water (b) and at least one water-soluble solvent (c) comprising a hydrophilic monomer in an amount of at least 10 wt % based on the total weight of the primer composition;
a coating composition having viscosity at 30° C. of 300 cP through 50,000 cP and including at least one monomer (d) and at least one photopolymerization initiator (e); and a surface smoothing composition including at least one polyfunctional monomer (f), at least one volatile solvent (g) and at least one photopolymerization initiator (h).

2. The dental coating kit according to claim 1, wherein the primer composition includes the acidic group-containing monomer (a) in an amount of 1 wt % through 90 wt %, the water (b) in an amount of 0.1 wt % through 90 wt % and the water-soluble solvent (c) in an amount of 10 wt % through 98 wt %, the coating composition includes the monomer (d) in an amount of 40 wt % through 99.99 wt % and the photopolymerization initiator (e) in an amount of 0.01 wt % through 10 wt % based on the monomer (d), and the surface smoothing composition includes the polyfunctional monomer (f) in an amount of 40 wt % through 98 wt %, the volatile solvent (g) in an amount of 1 wt % through 59 wt % and the photopolymerization initiator (h) in an amount of 0.01 wt % through 10 wt % based on a total weight of polymeric monomer(s) included in the surface smoothing composition.

3. The dental coating kit according to claim 1 or 2, wherein the coating composition further includes an inorganic filler with a refractive index of 1.9 or more and colloidal silica.

4. The dental coating kit according to claim 1, wherein the monomer (d) includes a hydrophobic monomer and a hydrophilic monomer, and the coating composition includes the hydrophilic monomer in an amount of 5 wt % through 50 wt %.

5. The dental coating kit according to claim 4, wherein the hydrophilic monomer is 2-hydroxyethyl methacrylate.

6. A dental coating method comprising applying, on a tooth, a primer composition including at least one acidic group-containing monomer (a), water (b), at least one water-soluble solvent (c) comprising a hydrophilic monomer in an amount of at least 10 wt % based on the total weight of the primer composition, and, optionally, at least one polymerization initiator;

forming a primer layer by drying or polymerically curing the primer composition;

applying, on the primer layer, a coating composition having viscosity at 30° C. of 300cP through 50,000 cP and including at least one monomer (d) and at least one photopolymerization initiator (e);

forming an intermediate layer by polymerically curing the coating composition through light irradiation;

applying, on the intermediate layer, a surface smoothing composition including at least one polyfunctional monomer (f), at least one volatile solvent (g) and at least one photopolymerization initiator (h); and forming a surface layer by polymerically curing the surface smoothing composition through light irradiation.

7. The dental coating method according to claim 6, wherein the tooth is a bleached tooth.

* * * * *